(12) United States Patent
Bansal et al.

(10) Patent No.: US 9,993,591 B2
(45) Date of Patent: Jun. 12, 2018

(54) EAR CLEANING DEVICE

(71) Applicant: Nupur Technologies, LLC, Buffalo, NY (US)

(72) Inventors: Rohan Bansal, Buffalo, NY (US); Joseph L. Priest, Lewiston, NY (US); Brij Bansal, Williamsville, NY (US); Ravinder K. Bansal, Clarence, NY (US)

(73) Assignee: Nupur Technologies, LLC, Buffalo, NY (US)

( * ) Notice: Subject to any disclaimer, the term of this patent is extended or adjusted under 35 U.S.C. 154(b) by 134 days.

(21) Appl. No.: 15/067,328

(22) Filed: Mar. 11, 2016

(65) Prior Publication Data

US 2016/0279321 A1 Sep. 29, 2016

Related U.S. Application Data

(60) Provisional application No. 62/137,304, filed on Mar. 24, 2015.

(51) Int. Cl.
*A61M 3/02* (2006.01)
*A61B 1/227* (2006.01)
*A61B 1/12* (2006.01)

(52) U.S. Cl.
CPC ........... *A61M 3/0216* (2014.02); *A61B 1/126* (2013.01); *A61B 1/128* (2013.01); *A61B 1/2275* (2013.01); *A61M 3/022* (2014.02); *A61M 3/0258* (2013.01); *A61M 2205/3368* (2013.01); *A61M 2205/3653* (2013.01); *A61M 2210/0662* (2013.01)

(58) Field of Classification Search
CPC ............ A61M 3/0233; A61M 2205/33; A61M 2205/36; A61M 2210/0662; A61B 1/06; A61B 1/227; A61B 1/04; A61B 1/2275
See application file for complete search history.

(56) References Cited

U.S. PATENT DOCUMENTS

| | | | | |
|---|---|---|---|---|
| 4,998,672 A | * | 3/1991 | Bordaz | B05B 7/32 239/307 |
| 5,170,779 A | | 12/1992 | Ginsberg | |
| 5,309,899 A | | 5/1994 | Ginsberg | |
| 5,527,275 A | * | 6/1996 | Ginsberg | A61M 3/02 601/155 |
| 5,869,954 A | * | 2/1999 | Kurz | H01H 9/547 200/16 R |
| 2005/0010084 A1 | * | 1/2005 | Tsai | A61B 1/00052 600/200 |
| 2005/0279197 A1 | * | 12/2005 | Wottreng, Jr. | B25B 23/045 81/469 |

(Continued)

*Primary Examiner* — Timothy J Neal
(74) *Attorney, Agent, or Firm* — Bond, Schoeneck & King, PLLC

(57) ABSTRACT

A system for cleansing a patient's ear is disclosed. The system includes a control unit, a portable applicator, and a liquid reservoir. The liquid reservoir includes a heater. The control unit includes controls for maintaining the temperature of the liquid in the reservoir within certain limits, for limiting the pressure of the liquid, and for varying the flow rate and pressure of the liquid. The portable applicator includes a hand piece, a nozzle connected to the fluid source and mounted on the hand piece, and a trigger for providing a flow control signal to the control unit.

10 Claims, 3 Drawing Sheets

(56) References Cited

U.S. PATENT DOCUMENTS

| | | | |
|---|---|---|---|
| 2006/0087283 A1* | 4/2006 | Phillips | B25F 5/00 320/114 |
| 2012/0059224 A1* | 3/2012 | Wellen | A61B 1/2275 600/200 |
| 2014/0166324 A1* | 6/2014 | Puzio | H01H 9/06 173/20 |

* cited by examiner

EAR CLEANING DEVICE

RELATED APPLICATION

This application claims the benefit of U.S. Provisional Application No. 62/137,304, filed on Mar. 24, 2015. The entire teachings of the above application are incorporated herein by reference.

BACKGROUND OF THE INVENTION

Devices for the irrigation of a person's ear or the removal of wax from the ear are generally known; however, such devices are not entirely satisfactory as many devices use a pressure regulator and solenoid valve combination to create a pulse stream of water. Thus, such prior devices do not provide an automated ear flushing system that readily and effectively controls the flow rate and pressure of the fluid delivered to the patient's ear in a comfortable manner.

SUMMARY OF THE INVENTION

In accordance with the present invention, an example system for cleaning a patient's ear may include a liquid reservoir, a portable applicator, and a control unit for modifying the flow of fluid from the applicator. The liquid reservoir includes a heater. The control unit includes a pump and controls for maintaining the temperature of the liquid within certain limits, for limiting the pressure of the liquid, and for varying the flow rate and pressure of the liquid. The portable applicator includes a hand piece, a nozzle connected to the fluid source and mounted on the hand piece, and a trigger for providing a signal to the control unit to control the flow rate.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Figure 3:
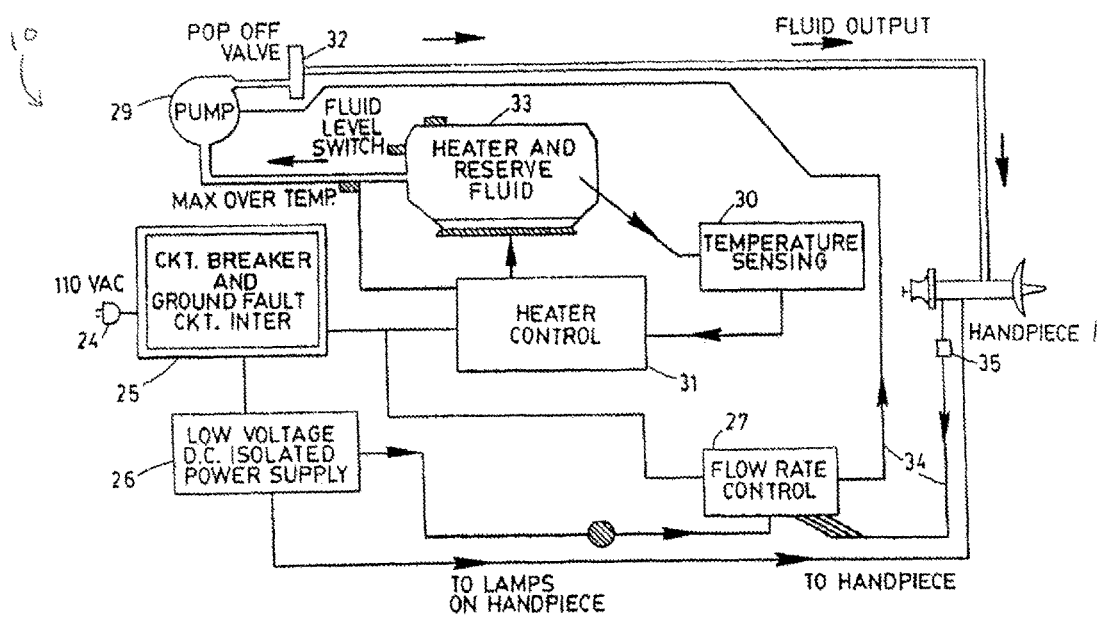
FIG. 3 is a block diagram illustrating a control unit of the system of FIG. 1, according to an example embodiment of the present invention.

The disclosed system includes a water reservoir that is assembled separately from the base of the system. A heating unit, integral to the reservoir, is controlled via one or more microcontrollers used to control the entire system. In alternative embodiments, the heating element may be an on-demand heating element that is in-line with the fluid supply line. A water pump is used to circulate water in order to maintain a constant temperature throughout the system. A control unit for controlling the pump speed is utilized, for example, by changing the voltage to the pump or by using pulse width modulation. Changing the pump speed allows for a reduction in noise caused by the pump, as well as increased pump life and reduced cost. The voltage applied to the pump may be changed, for example, during system warm-up or during standby. The method of flow control may include a linear potentiometer 35 as shown in FIG. 3, which senses a clinician's adjustment via a hand held applicator. The system may also incorporate multiple temperature and pressure sensors for redundancy and added safety.

The system enables a new method for cleaning ears by utilizing motor/pump control to vary the flow and pressure of water used to clean the ear. This is an improvement over previous systems that utilized a pressure regulator and solenoid valve combination to create a pulse stream of water. The system described herein not only greatly simplifies the controls but also eliminates the need for a pressure regulator and solenoid valve, resulting in a more reliable, effective, and cost-reducing system.

Figure 1:
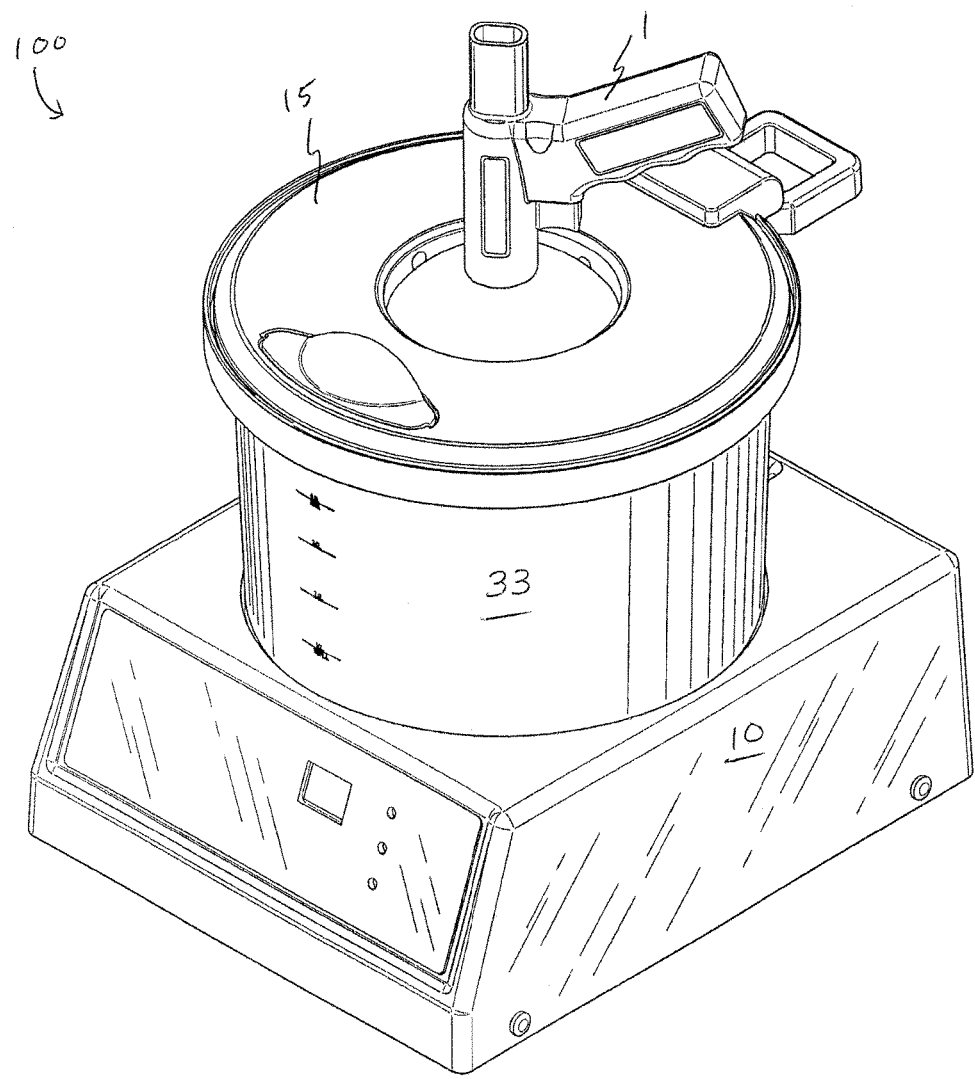
FIG. 1 is a schematic diagram illustrating a system for cleaning a patient's ear, according to an example embodiment of the present invention.

As shown in FIG. 1, an example embodiment of the system 100 includes a fluid reservoir 33 that is external from a control unit 10. The reservoir 33 may include an immersible heater that is disposed within the reservoir 33. The immersible heater may be controlled by the control unit 10 in the manner described below. The heater element may be an electric kettle style heating element, which heats the fluid in an efficient manner. The external reservoir 33 may be constructed of a material that is transparent (such as transparent acrylonitrile butadiene styrene (ABS) or transparent acrylic). Use of an external reservoir 33 facilitates the cleaning of the reservoir 33. The reservoir 33 may also include an integrated lid mechanism 15 to open the reservoir 33, which may include sensor(s) to confirm that the hand piece 1 is in place when docked in the reservoir 33. The integrated lid mechanism 15 can aid in the addition of water to the reservoir 33 and in cleaning of the reservoir 33.

Figure 2:
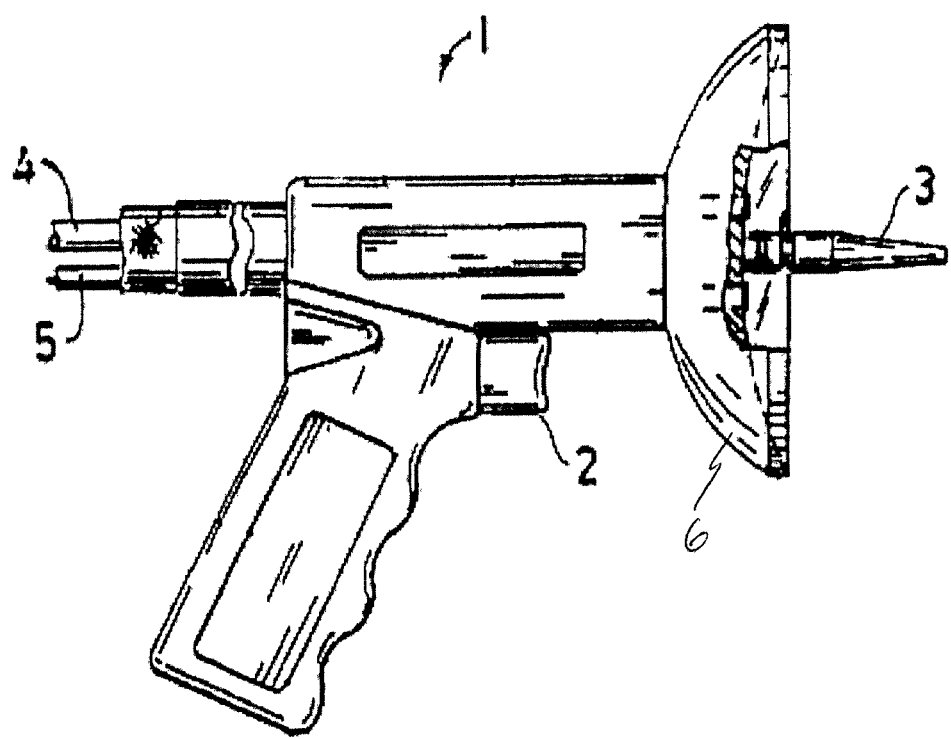
FIG. 2 is a schematic diagram illustrating a portable applicator of the system of FIG. 1, according to an example embodiment of the present invention.

An example portable applicator component 1 of the disclosed system is illustrated in FIG. 2. The body of hand piece 1 is preferably made from a plastic material, such as acrylonitrile-butadiene-styrene (ABS) plastic. As should be apparent to those skilled in the art, other suitable materials may be used. The hand piece includes a trigger 2 configured to send electronic signals to the control unit 10 for controlling the flow rate and pressure of the fluid.

At the application end of the hand piece unit 1 is a nozzle 3. A jet applicator nozzle is illustrated, but the nozzle style can be modified to provide a different flow pattern. Surrounding the nozzle area, and separating it from the body of the hand piece and from the operator, is a concave-convex disk transparent shield 6, which can be constructed of appropriate glass or plastic material. The shield 6 serves to contain the flow and reduce back splash while enabling an unobstructed view of the application of fluid flow to the patient's ear. The transparent shield 6 may further serve to facilitate viewing of the operating area by magnifying the transmitted light or image by virtue of appropriate shaping of the curvature of the disk as a magnifying lens. Viewing may be further enabled by lights located within the convex portion of the shield 6, which can transmit focused light using light-emitting diodes (LEDs), for example. The hand piece 1 may also include or be connected to a miniature video camera to, for example, enable real-time viewing of patient's ear canal and ear drum before, during, and after cleaning.

The hand piece 1 may be connected to the fluid reservoir 33 by a fluid line 4 (which provides a water flow pathway)

and line 5, which can enclose an electrical line (for transmitting electrical information from hand piece 1 to control unit). The water line 4 is preferably constructed of a plastic material which will not dissolve in water to any appreciable extent under the conditions of use. Thus, by way of illustration, one may use polyvinyl chloride tubing for the water line. Other suitable plastic materials should be apparent to those skilled in the art. A protective coating, such as a nylon sheath, for example, can be used to enclose lines 4 and 5, but is not necessary. Other conventional methods of enclosing the water line and/or the electrical lines may also be used or omitted altogether.

FIG. 3 illustrates a number of functions and advantages of the system including the fluid reservoir 33, the control unit 10, and the operatively connected hand piece applicator 1. The operations and connections shown are representational, with fluid pathways in double lines and electrical power and signal pathways in single lines.

The unit depicted in FIG. 3 is intended for ordinary operation in a medical office environment, and it is configured to be powered by a standard 110 volt, or 220 volt, alternating current power connector 24 through a safety circuit breaker 25 in the form of a modern ground fault low-voltage isolated direct current power supply 26 contained within the housing of the control unit 10. The water pump 29 may also be contained within the housing of the control unit 10.

The output of the low-voltage direct current power supply 26 is directed primarily to the flow-rate control 27, which is appropriately programmed to vary the flow rate signal to the water pump 29 that controls the flow output to application nozzle 3 (FIG. 2) at hand piece 1. Thus, the flow-rate control 27 receives the output signal 34 of the potentiometer from the hand piece 1 and generates an appropriate command to the water pump 29 to provide precisely indicated and controlled pressure and flow rates.

The separate fluid reservoir 33 (which is schematically represented and which contains a heater element, fluid level switch, and an appropriate temperature sensor) is in electrical communication with a temperature sensing unit 30 of the control unit, which is operatively connected to a heater control 31. Both the temperature sensing unit 30 and the heater control 31 operate the reservoir's heater when the temperature drops out of limits and can send a shutoff signal to the pump 29 if the fluid temperature is outside operating range, preventing flow to the patient until the fluid is the proper temperature. A pressure relief valve 32 may additionally be provided downstream of the pump for safety. Additional safety may be provided by setting the flow controller 27 to shut off the pump 29 if pressure exceeds a preset value.

The flow rate control 27 may be programmed and configured to control the rate and intensity of fluid injection, varying from slow and low pressure, increasing in linear fashion to a faster rate and higher pressure. Thus, maximum control and variability is placed in the practitioner's hands. It is the wide range of selectability of the flow and pressure characteristics of the water stream that, in the hands of a skilled operator, can most efficiently perform the cleansing process, even to the dislodgement of especially stubborn obstructions of ear wax, while maximizing patient comfort and virtually eliminating mishandled applications that have in the past caused many patients pain.

While this invention has been particularly shown and described with references to example embodiments thereof, it will be understood by those skilled in the art that various changes in form and details may be made therein without departing from the scope of the invention encompassed by the appended claims.

What is claimed is:

1. A system for cleaning a patient's ear, the system comprising:
    a fluid reservoir, a portable applicator, and a control unit;
    the fluid reservoir operatively connected to the control unit and including a heating device and a fluid supply line;
    the portable applicator operatively connected to the control unit and including a hand piece, a flow-directing orifice connected to the fluid supply line, the hand piece configured to generate an output signal to a flow rate controller of the control unit; and
    the control unit configured to maintain the temperature of fluid in the reservoir within preset limits and the control unit including a pump in signal communication with the flow rate controller, the control unit configured to limit the pressure and flow rate of the fluid through the portable applicator by generating a variable flow control signal with the flow rate controller in response to the output signal of the hand piece and variably controlling a flow output of the pump by setting an operating speed of the pump based on the variable flow control signal.

2. A system as in claim 1 wherein the hand piece is configured to generate the output signal in response to actuation of a control member of the portable applicator.

3. A system as in claim 2 wherein the control member includes a movable trigger.

4. A system as in claim 3 wherein the hand piece includes a linear potentiometer connected to the movable trigger that is configured to generate the output signal.

5. A system as in claim 1 wherein the pump is configured to circulate water through the fluid reservoir, fluid supply line, and the portable applicator when the portable applicator is mounted on the fluid reservoir.

6. A system as in claim 5 wherein the pump is configured to operate at a first speed during system warm-up and at a second speed during standby, the first speed being greater than the second speed.

7. A system as in claim 1 wherein the portable applicator includes a light source configured to illuminate the patient's ear.

8. A system as in claim 1 wherein the light source includes one or more light emitting diodes.

9. A system as in claim 1 wherein the portable applicator includes a video camera configured to view the patient's ear.

10. A system as in claim 1 wherein the control unit includes a video camera connected to an image receiving element mounted in the portable applicator.

* * * * *